US005691304A

United States Patent [19]
Kapa et al.

[11] Patent Number: 5,691,304
[45] Date of Patent: Nov. 25, 1997

[54] IMPROVED PROCESS FOR PREPARING POLYMYXIN B/DEXTRAN CONJUGATES

[75] Inventors: Prasad Kapa, Parsippany; Gleb Kardash, Rockaway; Andrew Kucerovy, Flanders; Philip Lake, Morris Plans; Paul G. Mattner, Piscataway; Russell C. Petter, Rockaway; Mahavir Prashad, Hopatcong; Sushil Sharma, Budd Lake, all of N.J.

[73] Assignee: Novartis AG, Basel, Switzerland

[21] Appl. No.: 449,436

[22] Filed: May 25, 1995

[51] Int. Cl.⁶ .............................. A61K 38/10; C07K 5/00
[52] U.S. Cl. ................................ 514/8; 530/317; 530/322
[58] Field of Search ............................... 514/8; 530/317, 530/322

[56] References Cited

U.S. PATENT DOCUMENTS 5,177,059  1/1993  Handley et al. ................ 530/317 X

OTHER PUBLICATIONS

Biotechnology Therapeutics, "*Inhibition of Polysaccharide–Induced TNF–Alpha Production by Semisynthetic Polymyxin–B Conjugated Dextran*", vol. 5, No. 3–4, 1994–1995, pp. 137–162, XP002015878, Coyne, C.P., et al.

*Primary Examiner*—Cecilia J. Tsang
*Assistant Examiner*—Anish Gupta
*Attorney, Agent, or Firm*—Carol A. Loeschorn; Carl W. Battle

[57] ABSTRACT

An improved process for producing a water-soluble polymyxin B/dextran conjugate comprises the step of reacting polymyxin B or pharmaceutically acceptable salt thereof with dextran in an aqueous media at a pH of about 9.3 to 10.

23 Claims, No Drawings

IMPROVED PROCESS FOR PREPARING POLYMYXIN B/DEXTRAN CONJUGATES

SUMMARY OF THE INVENTION

This invention relates to an improved process for producing a water-soluble conjugate of polymyxin B and dextran comprising the step of reacting polymyxin B or salt thereof with dextran in an aqueous media at a pH of about 9.3 to 10, more preferably at a pH of about 9.7. The preferred process involves reacting polymyxin B sulfate with oxidized dextran at a temperature of about 32° C. to covalently attach the polymyxin B molecule to the dextran through an amine bond. The conjugates prepared by the process of this invention are easily reproducible and exhibit significantly improved pharmacological properties, higher potency and increased endotoxin-neutralizing capacity.

BACKGROUND OF THE INVENTION

The medical need for an effective therapy for Systemic Inflammatory Response Syndrome (SIRS) and septic shock is widely recognized and the patient base is large with over 100,000 critical cases of SIRS/sepsis in developed nations requiring acute therapy and nearly 1 million patients at high risk for sepsis who could benefit from prophylaxis.

Endotoxin is recognized as the major initiator/primary mediator in the pathogenesis of SIRS/sepsis based upon a large body of human and animal studies; thus providing a clear scientific rationale for an anti-endotoxin approach to sepsis. Endotoxins or lipopolysaccharides are structural molecules derived from the cell walls of the Gram-negative bacteria. When introduced into the bloodstream, they can interfere with the regulation of body temperature and cause fever. They also have a toxic effect, leading to cardiac, pulmonary and kidney failure. Endotoxin-related diseases are a leading cause of death among those patients in intensive care units.

Unique among antibiotics is the ability of polymyxin B (PMB) to neutralize endotoxin, accomplished by binding to the lipid A region of the endotoxin molecule. Polymyxin B from B. polymyxa (B. aerosporus) is a highly charged amphiphilic cyclic peptidolipid. It is also useful in combating various fungal infections, especially those arising in immunocompromised individuals. However, PMB has some properties which renders it less than an ideal antibiotic. First, it has a short half-life in the body; requiring repeated dosages in order to be effective. Secondly, as it passes through the kidney it can cause extensive damage. Thirdly, at high doses it possesses neurotoxic properties which cause respiratory paralysis.

Previously, researchers have conjugated PMB to immobile or fixed molecules. See for example, Issekutz, 1983. J. Immunol. Methods 61:275-281, describing the binding of PMB to Sepharose. These conjugates, while useful in purification techniques, are not suitable for in vivo therapeutic use.

One approach to achieve pharmacological activity, increased duration, or decreased organ toxicity has involved the conjugation of drugs to large molecular weight macromolecules such as dextran, polyethylene glycol or polyvinylpyrrolidine. Attempts in this area of polymer conjugation have been met with only limited success, however. For example, the conjugated form of procainamide (an antiarrythmic drug) was less active and exhibited a shorter half life than native procainamide (Schact et al. 1985. Ann N.Y., Acad. Sci. 416:199-211). Similarly, a prostaglandin analog B245, linked to a carrier, was less effective (by several log orders) than the native molecule (Bamford et al. 1986, Bioch. Biophys. Acta 886:109-118). Reductions in biological potency have also been described for conjugated forms of kallikrein, aprotinin, bradykinin (Odya et al. 1978. Biochem. Pharmacol. 27:173-179), the anti-tumor drugs daunorubicin (Hurwitz et al. 1980, J. Appl. Biochecm. 2: 25-35), and mitomycin c (Takakura et al. 1984, Cancer Res. 44: 2505-2510). Conjugated enzymes also suffer a reduction in biological activity due to steric hindrance and reduced substrate accessibility (Blomhoff et al. 1983, Biochem. Biophys. Acta 757: 202-208; Marshall et al. 1976, J. Biol. Chem. 251(4): 1081-1087; R. L. Foster, 1975 Experimentia 31(7); 772-773; Wileman et al. 1983 J. Pharm. Pharmacol. 35: 762-765). There are however, some examples of improvements in circulatory half-life after conjugation (Wileman,supra: Kaneo 1989. Chem. Pharm. Bull. 37(1) 218-220).

It would be desirable to develop a form of PMB which would stay in the blood stream longer, and/or does not have neuro- or nephrotoxicity at therapeutic doses. U.S. Pat. No. 5,177,059 describes polymyxin B conjugates with polysaccharides (such as dextran), hydroxy ethyl starch, proteins such as albumin, and polymers such as polyvinylpyrrolidone, polyethylene glycol and polyvinyl alcohol. The '059 patent specifically describes a process for chemical conjugation of polymyxin B to dextran by reacting the materials at ambient temperature and pH 8.5-9.0.

The present invention is an improvement over the process described in U.S. Pat. No. 5,177,059, and provides a conjugate of polymyxin B and dextran which has surprisingly higher potency and improved pharmacological properties.

DETAILED DESCRIPTION

The present invention involves an improved process for producing a watersoluble conjugate of polymyxin B and dextran which is useful in treating fungal and bacterial infections and preventing disease caused by bacterial endotoxin. Specifically, the present invention relates to an improved process for producing the water soluble polymyxin B/dextran conjugate comprising the step of reacting polymyxin B or salt thereof with dextran in an aqueous media at a pH of about 9.3 to 10. Polymyxin B (PMB) is a peptide antibiotic and approved pharmaceutical agent with modest antibiotic activity. It has been in clinical use for over 40 years for topical and parenteral applications. Development of bacterial resistance to PMB is very rare. PMB binds endotoxin with an affinity of about $10^6$ $M^{-1}$ and can neutralize the biological effects of endotoxin from all clinically important gram-negative bacteria in a large number of in vitro and in vivo models. In vitro, it has been used as a standard to neutralize endotoxin. Moreover, in vivo, PMB protects against pathology of bacterial sepsis in many animal models such as acidosis and hypotension in enterobacterial infections and lethality due to gram-negative sepsis in dogs, rabbit, rats and mice. It also has potential in preventing sepsis in humans such as burn patients.

The PMB used for the preparation of the conjugate of this invention is available commercially from suppliers such as Pfizer. PMB is a topical and parenteral antibiotic in clinical use for many years and can be prepared by fermentation of *Bacillus polymyxa* (Prazmowski) Migula. PMB consists of a mixture of several related deca peptides. PMB or a pharmaceutically acceptable salt thereof is useful in this invention (such as polymyxin B sulfate and the like).

The dextran used in the process of this invention can be any of the conventional pharmaceutically-acceptable dextrans. Preferably the dextran is chemically modified to covalently bind to peptides, such as oxidized by an oxidizing agent (i.e., sodium periodate). The dextran should preferably have a weight average molecular weight of about 25,000 to 500,000; more preferably about 50,000 to 200,000; most preferably about 64,000 to 76,000. The molecular weight can be determined by gel permeation high performance liquid chromatography. The most preferred dextran is prepared by fermentation of *Leuconostoc mesenteroides* NRRL B-512. It is comprised of glucose units which are $\alpha[1-6]$-linked in a long linear chain with approximately 5% $\alpha[1-3]$ branching. Of the branched chains, about 85% have 1 to 2 glucose units and the remaining 15% an average of 33 units.

The general procedures for preparing conjugates of PMB and dextran in aqueous media are described in U.S. Pat. No. 5,177,059, (the disclosure of which is herein incorporated by reference) and are applicable to this invention. In a preferred embodiment of this invention, partially oxidized dextran is prepared by reaction with an oxidizing agent such as sodium periodate ($NalO_4$). This treatment creates aldehydes via oxidative cleavage of vicinal diols on the glucose monomers. Upon exposure of the partially oxidized dextran to PMB, Schiff's bases are formed. The production of conjugates within the scope of this invention requires careful control of the pH at about 9.3 to 10, preferably about 9.5 to 10, more preferably about 9.7, during the reaction of PMB and dextran, especially during the Schiff's base formation stage. The pH is preferably maintained using a borate buffer, especially one comprising sodium tetraborate. Also, preferably the temperature of the aqueous media is maintained at about 30° to 35° C. (more preferably about 32° C.) while reacting the PMB or salt thereof and dextran. The subsequent introduction of sodium borohydride ($NaBH_4$) reduces the Schiff's bases and remaining aldehydes to provide stable, covalent links (preferably through one or more amine bonds) between the PMB and dextran. The conjugate is preferably purified by ultrafiltration, such as using a 10,000 molecular weight cut-off membrane, to remove residual PMB, inorganic byproducts (e.g., borates), and potential low-molecular-weight degradation products. The pH of the aqueous media is preferably adjusted to about 5 to 7 prior to purification.

In the process of this invention, as well as in the conjugate produced thereby, the molecular ratio of PMB or salt thereof to dextran is about 1:15 to 200:1; more preferably about 1:2 to 1:5; most preferably about 1.5:5.

The PMB-dextran conjugate prepared according to this invention can be used in a manner consistent with the use of PMB itself; i.e., it can be used alone as an antibiotic for bacterial or fungal infections or combined with other bacteriocidal agents and/or anti-inflammatory agents. It may be administered in any of the forms by which native PMB is conventionally administered; i.e., intramuscularly, intravenously, intrathecally, subconjunctivally or topically. Thus, formulations for intramuscular injections typically comprise an effective amount of PMB-conjugate in sterile water, physiological saline or approximately 1% procane HCl. Intravenous formulations typically comprise an effective amount of PMB-conjugate in 5% dextrose and sterile water. Intrathecal formulations typically comprise an effective amount of PMB-conjugate in physiologic saline. For topical ophthalmic use, an effective amount can be mixed with water or physiologic saline, and optionally glycerine, and cupric sulfate for eye drops, or it may be made into an ointment or suspension. Creams, for topical applications, especially for burned areas, typically comprise an effective amount of PMB-conjugate in a base of inactive ingredients such as liquid petrolatum, propylene glycol, polyoxyethylene, polyoxypropylene, and emulsifying wax.

The purified PMB-dextran conjugates of this invention are essentially non-toxic. The amount of PMB-dextran conjugate of this invention to be used can be determined based on the amount of native PMB which would typically be prescribed for a particular patient (taking into account such factors as the condition being treated, and age and weight of the patient), and the activity of the particular PMB-conjugate used. A dosage reduction of one-half or more compared to native PMB can be realized due to the effective increased activity of the PMB conjugate, its reduced toxicity and its increased duration of activity.

The invention is better illustrated by reference to the following non-limiting Examples.

EXAMPLE 1

A). Oxidation Of Dextran

A 5-liter, 4-necked round-bottomed flask was charged with 2.310 liters of water for injection and 150 grams of dextran. The mixture was stirred at 21°–24° C. at approximately 140 RPM to effect dissolution. A solution of 3.9 grams of sodium periodate in 60 milliliters of water for injection was added (mild exotherm, approximately 1° C. The addition funnel was rinsed with 30 milliliters of water for injection. The resulting mixture was stored at 21°–24° C. for 1 hour. The solution was vacuum filtered through a 0.22μ Corning cellulose acetate 90 millimeter membrane filter and warmed to 30°–32° C. and maintain temperature.

B). Preparation of polymyxin B Sulfate/Borate Buffer Solution

This preparation was started 45 minutes prior to the completion of the dextran oxidation, filtration and warming from A) above. A 12-liter, 4-necked round-bottomed flask charged with 3.00 liter of pH 9.7 borate buffer*, and the temperature of the buffer was adjusted to 32° C. Next 45 grams of polymyxin B sulfate was added, and the resulting suspension was stirred at 32° C. for 45 minutes, The pH of the mixture was measured (initially 9.4) and adjusted to pH 9.7 at 32° C. by adding 30 milliliters of 5N NaOH.

C). Reaction of polymyxin B Sulfate with Oxidized Dextran

The pre-warmed (30°–32° C.), oxidized dextran solution (from part A) was added as fast as possible to the stirred mixture of polymyxin B sulfate in borate buffer at 32° C. (from part B). After the addition was complete, the pH of the mixing was measured (initially 9.5) and adjusted to pH 9.7 by adding 18 milliliters 5N NaOH. The mixture was stirred at 32° C. for 1 hour. To the heterogeneous mixture was added a solution of 3.6 grams of sodium borohydride in 50 milliliters of water for injection. The mixture was stirred at 32° C. for 2 hours. To the mixture was added another freshly prepared solution of 3.6 grams of sodium borohydride in 50 milliliters of water for injection. The mixture was stirred for 2 hours at 32° C. To the mixture was added a solution 3.6 grams of sodium borohydride in 50 milliliters of water. The heating was removed and the reaction mixture was allowed to cool to ambient temperature with stirring over 14 hours. The pH of the reaction mixture was measured (10.0) and adjusted to pH 5.7 by the addition of 1.27 liters of 1N HCl. The resulting mixture was stirred for 10 minutes after acidification, and the resulting mixture was vacuum filtered through a sterile 0.22μ Corning cellulose acetate membrane filter to produce 6.81 liters of a solution of polymyxin B-dextran conjugate which is held for purification via ultrafiltration.

D. Purification

The solution of polymyxin B-dextran conjugate (from part C) was purified using a pre-treated Areicon CH2PRS Ultrafiltration Unit with S1Y10 membrane cartridges. The purified product is removed from the ultrafiltration unit and stored frozen (−25° C.).

Analysis of the conjugate showed the following:

$IC_{50}$=16.8 µg/ml

% Activity=124.7

Dextran content=65.37 mg/ml

Total polymyxin B content=2.47 mg/ml

% Free polymyxin B=0.65

Ratio PMB: dextran=37.71 mg PMB/g dextran

*(The borate buffer was prepared as follows: a heat treated 5-L, 4-necked round-bottomed flask was charged with 114.3 g of sodium tetraborate, decahydrate and 2.906 L (2.906 kg) of water for injection. The solution was heated to 32° C. and the pH adjusted to 9.7 (initially 9.3) by adding 37 mL of 5N NaOH. The solution was vacuum filtered through a sterile 0.22µ Corning cellulose acetate 90 mm membrane filter and stored.)

EXAMPLE 2

The preparation process of Example 1 was repeated to yield a polymyxin B-dextran conjugate having the following analysis:

$IC_{50}$=16.4 µg/mL

% Activity=125.8

Dextran Content=65.30 mg/ml

Total polymyxin B=2.49 mg/ml

% Free polymyxin B=0.67

Ratio PMB:dextran=38.06 mg PMB/g dextran

EXAMPLE 3

Polymyxin B/dextran conjugates were prepared according to the process of Example 1 (except as indicated) to determine the effects of temperature. Payload (mg PMB/g dextran), average $IC_{50}$ (µg/ml) and % Active were determined and the results are presented in Table 1.

TABLE 1

EFFECT OF TEMPERATURE

| Sample No. | Conditions* | Payload (mg-PMB/gDextran) | Average $IC_{50}$ (µg/mL) | % Active |
|---|---|---|---|---|
| 1595-214-15 | 10 g PMB, 0.65 g NaIO$_4$, pH 9.7, 35° C. | 15.87 | 25.18 | 99.7 |
| 1595-222-10 | 10 g PMB, 0.65 g NaIO$_4$, pH 9.7, 35° C. | 19.81 | 26.07 | 91.1 |
| 1595-228-14 | 10 g PMB, 0.65 g NaIO$_4$, pH 9.7, 35° C. | 18.58 | 27.67 | 85.0 |
| 1595-233-28 | 10 g PMB, 0.65 g NaIO$_4$, pH 9.7, 10° C. | 49.53 | 143.83 | 23.6 |
| 1595-240-25 | 10 g PMB, 0.65 g NaIO$_4$, pH 9.7, 10° C. | 54.95 | 187.87 | 9.5 |
| 1595-245-39 | 10 g PMB, 0.65 g NaIO$_4$, pH 9.7, 10° C. | 56.03 | 195.7 | 10.8 |

*50 grams dextran

EXAMPLE 4

Polymyxin B/dextran conjugates were prepared according to the process of Example 1 (except as indicated) to determine the effect of the pH of the reaction between polymyxin B and dextran. Payload, average $IC_{50}$ and % Active were determined as in Example 3, and the results are presented in Table 2.

TABLE 2

Effect of pH at 32° C., 15 g PMB, 1.3 g NaIO$_4$, 50 g Dextran

| Sample No. | pH of reaction | Payload (mgPMB/gDextran) | Average IC50 (µg/mL) | % Active |
|---|---|---|---|---|
| 1499-276-30 | 4.0[a] | 2.36 | ND | ND |
| 1645-225-40 | 5.0[a] | 14.34 | ND | ND |
| 1499-299-10 | 7.0[b] | 15.26 | ND | ND |
| 1499-300-20 | 7.0[b] | 16.09 | 164.4 | 11.0 |
| 1649-2-10 | 8.0[b] | 32.03 | 107.7 | 17.8 |
| 1649-4-20 | 8.0[b] | 29.51 | 139.4 | 13.8 |
| 1645-131-10 | 8.5[c] | 69.94 | 74.5 | 24.9 |
| 1649-14-30 | 9.0[c] | 50.99 | 22.6 | 95.3 |
| 1645-114-10 | 9.0[c] | 50.16 | 22.5 | 88.6 |
| 1649-23-10 | 9.3[c] | 43.33 | 19.4 | 94.0 |
| 1645-135-40 | 9.3[c] | 39.96 | 19.0 | 95.8 |
| 1649-20-10 | 9.5[c] | 38.22 | 17.5 | 100.5 |
| 1645-141-30 | 9.5[c] | 39.9 | 17.8 | 98.1 |
| 1499-272-10 | 9.7[c] | 36.74 | 15.8 | 133.2 |
| 1645-13-44 | 9.7[c] | 34.99 | 14.9 | 148.9 |
| 1649-17-40 | 10.0[c] | 31.89 | 18.7 | 97.3 |

[a] Acetate buffer;
[b] Phosphate buffer;
[c] Borate buffer
ND: Samples were too dilute to determine these parameters

We claim:

1. An improved process for producing a water-soluble conjugate of polymyxin B and dextran comprising the step of reacting polymyxin B or a pharmaceutically acceptable salt thereof with dextran in an aqueous media at a pH of 9.3 to 10.

2. The process of claim 1 wherein said pH is 9.5 to 10.

3. The process of claim 1 wherein said aqueous media is maintained at a temperature of about 30° to 35° C. while reacting said polymyxin B or salt thereof and dextran.

4. The process of claim 3 wherein said temperature is about 32° C.

5. The process of claim 1 wherein said step of reacting polymyxin B or salt thereof with dextran comprises covalently attaching said polymyxin B or salt thereof to said dextran through one or more amine bonds.

6. The process of claim 1 wherein said polymyxin B salt is polymyxin B sulfate.

7. The process of claim 1 wherein the molecular ratio of said polymyxin B or salt thereof to said dextran is about 1:15 to 200:1.

8. The process of claim 7 wherein said molecular ratio of polymyxin B or salt thereof to dextran is about 1:2 to 1:5.

9. The process of claim 7 wherein said molecular ratio of polymyxin B to dextran is about 1.5:5.

10. The process of claim 1 wherein said dextran has a weight average molecular weight of about 25,000 to 500,000.

11. The process of claim 1 wherein said dextran has a weight average molecular of about 50,000 to 200,000.

12. The process of claim 1 wherein said dextran has a weight average molecular weight of about 64,000 to 76,000.

13. The process of claim 1 wherein said dextran has been partially oxidized.

14. The process of claim 13 wherein said dextran has been partially oxidized using sodium periodate.

15. The process of claim 1 wherein said pH is maintained using a borate buffer.

16. The process of claim 15 wherein said borate buffer comprises sodium tetraborate.

17. The process of claim 1 comprising subsequent reaction with sodium borohydride.

18. The process of claim 1 additionally comprising subsequently adjusting the pH of said aqueous media to about 5 to 7 and purifying said resulting conjugate.

19. The process of claim 18 wherein said conjugate is purified via ultrafiltration.

20. The process of claim 1 wherein said pH is about 9.7.

21. A water-soluble conjugate of polymyxin B or a pharmaceutically acceptable salt thereof and dextran produced by the process of claim 1.

22. An improved process for producing a water-soluble conjugate of polymyxin B and dextran comprising:

a) preparing partially oxidized dextran by reacting dextran with sodium periodate, b) reacting polymyxin B or a pharmaceutically acceptable salt thereof with dextran in an aqueous media at a pH of 9.3 to 10 and a temperature of about 30° to 35° C., c) adding sodium borohydride to the resultant aqueous media from step b), and d) purifying the resultant polymyxin B-dextran conjugate.

23. A water-soluble conjugate of polymyxin B or a pharmaceutically acceptable salt thereof and dextran produced by the process of claim 22.

* * * * *